United States Patent
Hu et al.

(10) Patent No.: US 10,602,757 B2
(45) Date of Patent: Mar. 31, 2020

(54) NUTRITION SUPPLEMENT FOR ANIMAL AND USE THEREOF

(71) Applicant: BIOFORTE BIOTECHNOLOGY(SHENZHEN) CO., LTD., Guangdong (CN)

(72) Inventors: Wenfeng Hu, Guangdong (CN); Xu Pang, Guangdong (CN); Chujun Li, Guangdong (CN); Haiyong Zhou, Guangdong (CN); Jianfeng Zhu, Guangdong (CN)

(73) Assignee: BIOFORTE BIOTECHNOLOGY(SHENZHEN) CO., LTD., Guangdong (CN)

( * ) Notice: Subject to any disclaimer, the term of this patent is extended or adjusted under 35 U.S.C. 154(b) by 103 days.

(21) Appl. No.: 15/553,579

(22) PCT Filed: Dec. 15, 2016

(86) PCT No.: PCT/CN2016/110202
§ 371 (c)(1),
(2) Date: Aug. 24, 2017

(87) PCT Pub. No.: WO2018/107445
PCT Pub. Date: Jun. 21, 2018

(65) Prior Publication Data
US 2019/0090509 A1    Mar. 28, 2019

(51) Int. Cl.
| | | |
|---|---|---|
| *A23K 50/40* | (2016.01) | |
| *A01K 67/033* | (2006.01) | |
| *A23K 20/147* | (2016.01) | |
| *A23K 50/60* | (2016.01) | |
| *A23K 50/80* | (2016.01) | |
| *A23K 50/75* | (2016.01) | |
| *A23K 50/00* | (2016.01) | |

(52) U.S. Cl.
CPC ............ *A23K 50/40* (2016.05); *A01K 67/033* (2013.01); *A23K 20/147* (2016.05); *A23K 50/00* (2016.05); *A23K 50/60* (2016.05); *A23K 50/75* (2016.05); *A23K 50/80* (2016.05); *A23V 2002/00* (2013.01); *Y02A 40/818* (2018.01)

(58) Field of Classification Search
None
See application file for complete search history.

(56) References Cited

U.S. PATENT DOCUMENTS

| | | | | |
|---|---|---|---|---|
| 6,086,878 A | * | 7/2000 | Adalsteinsson | C07K 16/02 424/157.1 |
| 2005/0266052 A1 | * | 12/2005 | Bartlett | A23K 10/22 424/442 |

FOREIGN PATENT DOCUMENTS

CN    106509506 A  *  3/2017

OTHER PUBLICATIONS van Huis A, Edible insects: future prospects for food and feed security, Food and Agriculture Organization of the United Nations (Year: 2013).*
Makkar et al (Animal Feed Science and Technology 197 (2014) 1-33) (Year: 2014).*

* cited by examiner

Primary Examiner — Celeste A Roney
(74) Attorney, Agent, or Firm — JCIPRNET

(57) ABSTRACT

The present invention belongs to a technical field of nutrition additives for animal, and specifically discloses a nutrition supplement for animal, comprising eggs of an edible insect. Further, the eggs of the edible insect are one or more of eggs of *Hermetia illucens* L., eggs of *Tenebrio molitor* and eggs of fly. The present invention finds that the eggs of edible insect provide better effects such as enhancing nutrition, promoting growth and health care for animals, especially for newborn animals, weaning animals, weak animals or sick animals. The nutrition supplement provided by the present invention can be prepared easily and used conveniently. The present invention using the eggs of edible insect as a main component of the nutrition supplement can not only improve a health level of animals including livestock, aquatic animals and the like, but also enhance a feed intake, a feed conversion level and a comprehensive benefit of cultivation with a good application prospect.

12 Claims, No Drawings

NUTRITION SUPPLEMENT FOR ANIMAL AND USE THEREOF

CROSS-REFERENCE TO RELATED APPLICATION

This application is a 371 international application of PCT application serial no. PCT/CN2016/110202, filed on Dec. 15, 2016. The entirety of the above-mentioned patent application is hereby incorporated by reference herein and made a part of this specification.

TECHNICAL FIELD

The present invention belongs to a technical field of a nutrition additive for animals, and more specifically relates to a nutrition supplement for animals and use thereof.

BACKGROUND

With a high-speed development of animal husbandry, aquaculture and pet economy, the industry pays more and more attention to nutrition and health of livestock, aquatic animals and pets, as well as their quality of life and health, which promotes a development of efficient nutrition supplement product, for example, development and application of protein powder, fat powder, high-energy nutrition paste and the like.

Common nutrition supplement for animals is made of protein, fat and nucleic acids which derive from animal, plant and microorganisms. Nowadays, protein and fat from an animal source generally used for preparing nutrition supplement are mainly derived from milk protein, whey protein, plasma protein and viscera such as liver, intestine membrane and the like. Protein and fat from a botanic source are mainly derived from seeds or processed byproducts of oil plants such as soybean. A microorganism source mainly comprises yeast paste and algae powder which are rich in protein, fat and nucleic acids and made by processing yeast powder and microalgae.

An edible insect protein will be a source of protein and fat of new type animal feed. In May 2013, Food and Agriculture Organization of the United Nations (FAO) published a report, Edible Insect, Future Expectations of Food and Feed Safety, which strongly advocated that every country should develop edible insects as a source of new type protein and fat for human or animal consumption respectively in the future to reduce dependence on lands, forest deterioration and an emission of greenhouse gas. On the other hand, the insect protein is abundant in antibacterial peptide, and fat which has a high concentration of lauric acid, and unknown growth factors. The insect protein presents a positive influence on the growth and health of human and farmed animals.

A dried insect larva comprises 40% or more of protein and rational amino acids composition, which is suitable for cultivating poultry and aquatic animals. There is a great variety of fatty acids in insect fat, including more than ten kinds of saturated fatty acids, unsaturated fatty acids and polyunsaturated fatty acids. The saturated fatty acids can be lauric acid, palmitic acid and the like, the unsaturated fatty acids can be oleic acid and the like and the polyunsaturated fatty acids can be linoleic acid and the like.

Insect serving as a new type feed protein has been just started. The content of insect protein in so called insect feed protein raw material which was just launched to market at present is low and is mainly compound with vegetable protein and conventional animal protein. Besides, the content of fatty acids is relatively low. Moreover, the nutrition supplement for newborn animals still consists of proteins and fat from conventional animal source and botanic source, which is unable to provide sufficient nutrition effectively for the newborn animals to grow fast.

In view of this, the present invention has developed the nutrition supplement product with more abundant nutrition and higher efficiency to solve the above problems.

SUMMARY OF THE INVENTION

An objective of the present invention is to provide a new nutrition supplement for animal according to deficiencies of prior art.

According to our research, it is found that nutrition of eggs of insect is more abundant. Compared with a larva, an imago or a pupa of insects, concentrations of protein, fat and unknown growth factors contained in the eggs of insect are higher, with outstanding effects especially on growth and health care of a newborn animal as well as a weak animal and on rescue of a sick animal. These animals include newborn suckling piglets, weak piglets, cad pigs and the like, newborn poultry such as chicks and ducks, aquatic animals and pets.

Another objective of the present invention is to provide use of the above nutrition supplement for animal.

The objectives of the present invention are realized by following technical solutions:

A nutrition supplement for animal is provided in the present invention, comprising eggs of an edible insect.

Preferably, the eggs of the edible insect are one or more of eggs of *Hermetia illucens* L., eggs of *Tenebrio molitor* and eggs of fly.

Preferably, the nutrition supplement further comprises one or more of an other animal source nutrient, a botanic source nutrient, a microorganism source nutrient and a protective agent;

The other animal source nutrient is derived from one or more of cattle milk, sheep milk, fish meal, fish tallow, yolk, animal muscle and extracts of viscus; the botanic source nutrient is selected from one or more of substances consisting of soybean protein, soybean oil and corn steep liquor; the microorganism source nutrient comprises one or two of yeast extracts and microalgae extracts.

More preferably, the protective agent comprises one or more of skim milk, trehalose, glycerol and antioxidant.

Preferably, in percentage by weight, the eggs of edible insect account for 50%-90%, the other animal source nutrient accounts for 0%-10%, the botanic source nutrient accounts for 0%-10%, the microorganism source nutrient accounts for 0%-10% and the protective agent accounts for 0.1%-20%.

When the nutrition supplement comprises the eggs of insect, other animal source nutrient, botanic source nutrient, microorganism source nutrient and protective agent. Firstly, the eggs of edible insect are mixed with the protective agent, grinded at low temperature and then dried to be smashed, followed by being added with other animal source nutrient, botanic source nutrient and microorganism source nutrient, and being mixed evenly. Then they are dried to form a powder product with a moisture below 12%; or after being mixed evenly, they are prepared to form a paste product.

The present invention simultaneously claims use of above nutrition additives in preparing nutrition additives of animal feed.

Preferably, the nutrition supplement is added into animal feed or drinking water, or is artificially fed to the animal directly.

Preferably, the nutrition supplement is added into the animal feed or drinking water according to a proportion of 0.01-0.5% (w/w), or is directly fed in 1 g-5 g for every day.

Preferably, the animals include newborn animals, weaning animals, weak animals or sick animals.

Preferably, species of the animals include aquatic animals, livestock or pets.

Preferably, the aquatic animals include fish, shrimp, crab and the like. The livestock include pig, chicken, duck and the like. The pets include cat, dog, pet bird, reptile and the like.

In addition, the present invention simultaneously claims products in form of dry powder with low moisture or in form of paste with high moisture prepared by the eggs of edible insect.

The present invention simultaneously claims use of the nutrition supplement in preparing additives that control diarrhea of the newborn animals.

The present invention simultaneously provides use of the nutrition supplement in preparing additives that enhance a feed intake of animal.

The nutrition supplement of the present invention is used in a feed formula of newborn piglet of which an effect of weight gain is obvious and the feed intake is increased. Also, an occurrence of diarrhea that usually occurs in the piglet is greatly reduced.

The nutrition supplement of the present invention is used in a feed formula of layers of which a laying rate is enhanced, a qualified rate of egg is enhanced and the feed intake is promoted.

The nutrition supplement of the present invention is used in a feed formula of aquatic feed (for example *Lateolabrax japonicas*). The feed intake is enhanced, the *Lateolabrax japonicas* likes eating and a feed efficiency is increased.

Compared to the prior art, the present invention has following advantages and beneficial effects:

The eggs of edible insect are directly used as the nutrition supplement in the present invention which is easy to be prepared and can effectively enhance growth performance and health level of animals including livestock, aquatic animals and pets. Besides, the nutrition supplement provided by the present invention provides good control effects on the diarrhea problems that usually occur in the newborn animals. Meanwhile the nutrition supplement can obviously enhance the feed intake and a feed utilization, reduce a feed-meat conversion ratio or a feed-egg conversion ratio and enhance an overall benefit of cultivation.

DETAILED DESCRIPTION OF EMBODIMENTS

The present invention will be further described in combination with specific embodiments which do not limit the present invention in any way. Unless otherwise specified, reagents, methods and equipments used in the present invention are conventional reagents, methods and equipments in the art.

Unless otherwise specified, the reagents and materials used in the present invention are commercially available.

Embodiment 1: Eggs of *Hermetia illucens* L. Used as a Raw Material of a Nutrition Additive The eggs of *Hermetia illucens* L. were mixed with a protective agent, glycerol, followed by being grinded at low temperature. Then they were freeze dried, smashed and dried until a moisture is below 12%.

Embodiment 2: Application Effect (Aimed at Newborn Piglets)

General commercially available creep feed for piglet was mixed with 0.1% of a nutrition supplement prepared in Embodiment 1; one-week-old tri-crossbreeding piglets, as experimental animals, were fed for two weeks and compared with those fed with the general commercially available creep feed without adding the nutrition supplement. An experimental result is shown in Table 1:

TABLE 1

Effect of the nutrition additives on growth performance of newborn piglet

| | daily weight gain (g/d. each) | average feed intake of each (kg/d) | feed conversion ratio (feed intake/weight gain of piglet) | diarrhea rate (%) |
| --- | --- | --- | --- | --- |
| feed added with 0.1% of the nutrition supplement | 266.7 | 0.291 | 1.09 | 1.33% |
| commercially available creep feed | 197.2 | 0.270 | 1.37 | 5.24% |

It can be seen in Table 1 that compared to those fed with general creep feed, the weight gain and the feed intake of one-week-old tri-crossbreeding piglets which were fed with the feed added with 0.1% of the nutrition supplement, are enhanced. Intestinal health is improved. A disease incidence of diarrhea and the feed conversion ratio are decreased.

Embodiment 3: Application Effect (aimed at *Lateolabrax japonicas*)

The *Lateolabrax japonicas* was fed with general commercially available feed special for *Lateolabrax japonicas* which was mixed with 0.5% of the nutrition supplement prepared in Embodiment 1 for one month and compared with those fed with the general commercially available feed without adding the nutrition supplement. The experimental result is shown in Table 2:

TABLE 2

Effect of the nutrition additives on growth performance of *Lateolabrax japonicas*

| | survival rate (%) | feed efficiency (%) | specific growth rate (%/d) |
| --- | --- | --- | --- |
| feed added With 0.5% of the nutrition supplement | 98.13 | 0.94 | 0.93 |
| commercially available feed | 89.53 | 0.83 | 0.84 |

It can be seen from Table 2 that compared to those fed with general feed, the survival rate, the feed efficiency and the specific growth rate of *Lateolabrax japonicas* which was fed with the feed added with 0.5% of the nutrition supplement, are enhanced.

Embodiment 4: Application Effect (Aimed at Layers)

The layers were fed with general commercially available feed special for layers which was mixed with 0.05% of the nutrition supplement prepared in Embodiment 1 for one month and compared with those fed with the general commercially available feed without adding the nutrition supplement. The experimental result is shown in Table 3:

TABLE 3

Effect of the nutrition additives on growth performance of layers

| | laying rate (%) | feed intake of each (g) | qualified rate (%) |
|---|---|---|---|
| feed added with 0.05% of the nutrition supplement | 87.63 | 102.62 | 98.53 |
| commercially available feed | 80.36 | 91.51 | 96.62 |

It can be seen from Table 3 that compared to those fed with general feed, the laying rate, the feed intake of each and the qualified rate of egg for layers which were fed with the feed added with 0.05% of nutrition supplement, are enhanced with obvious effect.

Embodiment 5: Aimed at Newborn Piglets

A formula of the nutrition supplement is as follow: eggs of an edible insect accounting for 50%, bovine colostrum accounting for 10%, soybean protein accounting for 10%, yeast extracts accounting for 10% and glycerol accounting for 20%. 14-day-old tri-crossbreeding piglets were chosen to be fed with the general commercially available creep feed for piglets which was mixed with 0.1% of the nutrition supplement prepared in Embodiment 5 for two weeks and compared with those fed with the general commercially available feed without adding the nutrition supplement. The experimental result is shown in Table 4:

TABLE 4

Effect of the nutrition additives on growth performance of newborn piglet

| | everyday weight gain (g/d. each) | average feed intake of each (kg/d) | Feed-meat conversion ratio (feed intake/ weight gain of piglet) | diarrhea rate (%) |
|---|---|---|---|---|
| feed added with 0.1% of the nutrition supplement | 275.21 | 0.295 | 1.07 | 1.27% |
| commercially available feed | 202.19 | 0.253 | 1.25 | 3.14% |

It can be seen in Table 4 that compared to those fed with general feed, the weight gain and the feed intake of piglets which were fed with the nutrition supplement feed provided by the present invention, are enhanced. The intestinal health is improved. The disease incidence of diarrhea and the feed conversion ratio are decreased at the same time.

Embodiment 6: Aimed at Newborn Piglet

A formula of the nutrition supplement is as follow: the eggs of edible insect accounting for 70%, bovine colostrum accounting for 6%, soybean protein accounting for 6%, yeast extracts accounting for 6% and glycerol accounting for 12%. The newborn piglets were fed with the general commercially available feed special for newborn piglets which was mixed with 0.1% of the nutrition supplement prepared in Embodiment 6 for two weeks and compared with those fed with the general commercially available feed without adding the nutrition supplement. The experimental result is shown in Table 5:

TABLE 5

Effect of the nutrition additives on growth performance of newborn piglet

| | daily weight gain (g/d. each) | average feed intake of each (kg/d) | Feed-meat conversion ratio (feed intake/ weight gain of piglet) | diarrhea rate (%) |
|---|---|---|---|---|
| feed added with 0.1% of nutrition supplement | 291.21 | 0.326 | 1.12 | 2.27% |
| commercially available feed | 223.19 | 0.299 | 1.34 | 5.14% |

It can be seen in Table 5 that compared to those fed with general feed, the weight gain and the feed intake of piglets which were fed with the nutrition supplement feed provided by the present invention, are enhanced. The intestinal health is improved. The disease incidence of diarrhea and the feed conversion ratio are decreased at the same time.

Comparative Embodiment 1

Experiment conditions are the same as Embodiment 2. Compared with other nutrition supplements of Embodiments 1-6, a formula is shown as follow:

bovine colostrum from animal source accounting for 60%, soybean protein from botanic source accounting for 35%, yeast extracts from microorganism accounting for 10%. The effects are shown in Table 6:

TABLE 6

Using effects of nutrition supplement in Comparative Embodiment 1

| | daily weight gain (g/d. each) | average feed intake of each (kg/d) | feed conversion ratio (feed intake/ weight gain of piglet) | diarrhea rate (%) |
|---|---|---|---|---|
| feed added with 0.1% of the nutrition supplement of Comparative Embodiment 1 | 235.6 | 0.285 | 1.21 | 3.33% |

Comparative Embodiment 2

A commercially available dried larva of *Hermetia illucens* L. was used as the nutrition supplement. It was added in a weight percentage of 0.1% into the commercially available feed special for newborn piglets and fed to the newborn piglets for two weeks. The test results are shown in Table 7:

TABLE 7

Influence of the nutrition supplement of Comparative Embodiment 2 on growth performances of newborn piglet

| | daily weight gain (g/d. each) | average feed intake of each (kg/d) | Feed-meat conversion ratio (feed intake/ weight gain of piglet) | diarrhea rate (%) |
|---|---|---|---|---|
| feed added with 0.1% of the nutrition supplement of Comparative Embodiment 2 | 232.7 | 0.280 | 1.18 | 2.33% |

It can be seen in Table 7 that using the nutrition supplement added with 0.1% of the dried larva of *Hermetia illucens*L. is compared with using eggs of *Hermetia illucens*L. as the nutrition supplement in Embodiment 2. The weight gain, the feed intake and a feed utilization of the latter are obviously improved, also the diarrhea rate is reduced.

Obviously, the above embodiments are only examples for clearly specifying the present invention but not for limiting the implementations. For those skilled in the art, changes or variations in different forms based on above can still be made. It is unnecessary or unable to give all implementations here. And obvious changes or variations extended hereby are still within the scope of the present invention.

What is claimed is:

1. A composition comprising:
   a nutrition supplement for animals which contains eggs of an edible insect.

2. The composition supplement of claim 1, wherein the edible insect is *Hermetia illucens* L., *Tenebrio molitor*, fly, or any combinations thereof.

3. The composition of claim 2, further comprising an other-animal source nutrient, a botanic source nutrient, a microorganism source nutrient, a protective agent, or any combination thereof.

4. The composition of claim 3, wherein
   the other-animal source nutrient is derived from cattle milk, sheep milk, fish meal, fish tallow, yolk, animal muscle, extracts of animal viscus, or any combination thereof,
   the botanic source nutrient is soybean protein, soybean oil, corn steep liquor, or any combination thereof, and
   the microorganism source nutrient is yeast extracts, microalgae extracts, or any combination thereof.

5. The composition supplement of claim 3, wherein the protective agent is skim milk, trehalose, glycerol, antioxidant, or any combination thereof.

6. The composition of claim 3, wherein composition comprises:
   50-90 wt % of the eggs of the edible insect;
   0-10 wt % of the other-animal source nutrient;
   0-10 wt % of the botanic source nutrient;
   0-10 wt % of microorganism source nutrient; and
   0.1-20 wt % of protective agent.

7. A preparation method of a composition, comprising:
   preparing a nutrition supplement for animals by mixing eggs of an edible insect, with a protective agent to form a mixture;
   grinding the mixture;
   drying and then smashing the grinded mixture to form a final dry powder mixture; and
   mixing the dry powder mixture with an other-animal source nutrient, a botanic source nutrient, a microorganism source nutrient, or any combination thereof to form a paste product.

8. The preparation method of claim 7, further comprising:
   drying the final mixture until the water content is less than 12% to form a powder product.

9. A method of preparing an animal feed, comprising:
   adding 0.01-0.5 wt % of the composition of claim 5 to an animal feed to form a uniform mixture.

10. A method of feeding an animal, comprising:
    feeding an animal with an animal feed or a drinking water comprising 0.01-0.5 wt % of the composition of claim 5, or directly with the composition claim 5.

11. The method of claim 10, wherein the animal is a newborn animal, a weaning animal, a weak animal, a sick animal, or any combination thereof.

12. The method of claim 10, wherein the animal is an aquatic animal, a livestock, or a pet.

* * * * *